US012310782B2

United States Patent
Noda et al.

(10) Patent No.: US 12,310,782 B2
(45) Date of Patent: May 27, 2025

(54) X-RAY IMAGE PROCESSING APPARATUS, X-RAY DIAGNOSIS APPARATUS, METHOD, AND STORAGE MEDIUM

(71) Applicant: CANON KABUSHIKI KAISHA, Tokyo (JP)

(72) Inventors: Takeshi Noda, Kanagawa (JP); Katsuro Takenaka, Saitama (JP); Haruki Iwai, Tochigi (JP); Daisuke Sato, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 293 days.

(21) Appl. No.: 17/938,286

(22) Filed: Oct. 5, 2022

(65) Prior Publication Data
US 2023/0104524 A1  Apr. 6, 2023

(30) Foreign Application Priority Data
Oct. 6, 2021  (JP) ................. 2021-165048

(51) Int. Cl.
*A61B 6/58* (2024.01)
*A61B 6/00* (2024.01)
*A61B 6/40* (2024.01)
*A61B 6/50* (2024.01)

(52) U.S. Cl.
CPC ............. *A61B 6/585* (2013.01); *A61B 6/405* (2013.01); *A61B 6/482* (2013.01); *A61B 6/502* (2013.01); *A61B 6/505* (2013.01)

(58) Field of Classification Search
CPC ......... A61B 6/585; A61B 6/405; A61B 6/482; A61B 6/502; A61B 6/505; A61B 6/5217; A61B 6/5235
See application file for complete search history.

(56) References Cited

U.S. PATENT DOCUMENTS

| 6,052,433 A | * | 4/2000 | Chao | .................... A61B 6/4241 378/98.12 |
| 2005/0109927 A1 | * | 5/2005 | Takenaka | .............. G01T 1/2928 250/252.1 |
| 2008/0310580 A1 | * | 12/2008 | Takahashi | .............. A61B 6/037 378/19 |

(Continued)

FOREIGN PATENT DOCUMENTS

| JP | 2002-200071 A | 7/2002 |
| JP | 2005-169068 A | 6/2005 |

(Continued)

*Primary Examiner* — Blake C Riddick
(74) *Attorney, Agent, or Firm* — Canon U.S.A., Inc. IP Division

(57) ABSTRACT

An X-ray image processing apparatus comprising: a first obtaining unit configured to obtain a first X-ray image including an object; a second obtaining unit configured to obtain a first measured value associated with an X-ray condition of the first X-ray image, a second X-ray image that does not include the object, and a second measured value associated with an X-ray condition of the second X-ray image; a gain correction unit configured to correct the first X-ray image based on the first measured value, the second X-ray image, and the second measured value; and an image generation unit configured to generate an evaluation image for evaluating a state of the object based on a corrected image that is the first X-ray image corrected by the gain correction unit.

16 Claims, 9 Drawing Sheets

(56) References Cited

U.S. PATENT DOCUMENTS

| | | | |
|---|---|---|---|
| 2009/0296884 A1* | 12/2009 | Honda | A61B 6/505 378/62 |
| 2010/0034450 A1* | 2/2010 | Mertelmeier | A61B 6/482 378/21 |
| 2011/0206183 A1* | 8/2011 | Tanaka | A61B 6/0487 378/62 |
| 2012/0076377 A1* | 3/2012 | Dutta | G16H 50/30 378/207 |
| 2012/0207270 A1* | 8/2012 | Flohr | G06T 5/50 378/5 |
| 2013/0022170 A1* | 1/2013 | Cho | A61B 6/482 378/62 |
| 2013/0343521 A1* | 12/2013 | Lee | A61B 6/563 378/62 |
| 2014/0086383 A1* | 3/2014 | Huwer | A61B 6/5211 378/5 |
| 2015/0348292 A1* | 12/2015 | Taguchi | G06T 11/005 382/131 |
| 2016/0000396 A1* | 1/2016 | Taguchi | G06T 5/70 382/131 |
| 2016/0007943 A1* | 1/2016 | Hoernig | G06T 5/50 378/37 |
| 2016/0262714 A1* | 9/2016 | Krauss | A61B 6/544 |
| 2017/0027534 A1* | 2/2017 | Oh | G16H 50/30 |
| 2017/0086769 A1* | 3/2017 | Allmendinger | A61B 6/032 |
| 2017/0340305 A1* | 11/2017 | Bertens | G06T 7/337 |
| 2018/0021000 A1* | 1/2018 | Akiyama | A61B 6/06 378/62 |
| 2018/0078230 A1* | 3/2018 | Hoernig | A61B 6/469 |
| 2018/0192977 A1* | 7/2018 | Jin | G01V 5/22 |
| 2018/0199904 A1* | 7/2018 | Ganguly | A61B 6/482 |
| 2019/0038918 A1* | 2/2019 | Lu | A61B 6/4241 |
| 2019/0053771 A1* | 2/2019 | Butani | A61B 6/502 |
| 2020/0196975 A1* | 6/2020 | Vancamberg | A61B 5/0064 |
| 2020/0236303 A1* | 7/2020 | Machida | H04N 25/683 |
| 2021/0279917 A1* | 9/2021 | Wilk | A61B 6/5282 |
| 2023/0038970 A1* | 2/2023 | Mackie | A61B 6/4208 |
| 2023/0218254 A1* | 7/2023 | Fukuda | G06T 5/50 378/37 |

FOREIGN PATENT DOCUMENTS

| | | |
|---|---|---|
| JP | 2011-245117 A | 12/2011 |
| JP | 2019-126581 A | 8/2019 |

* cited by examiner

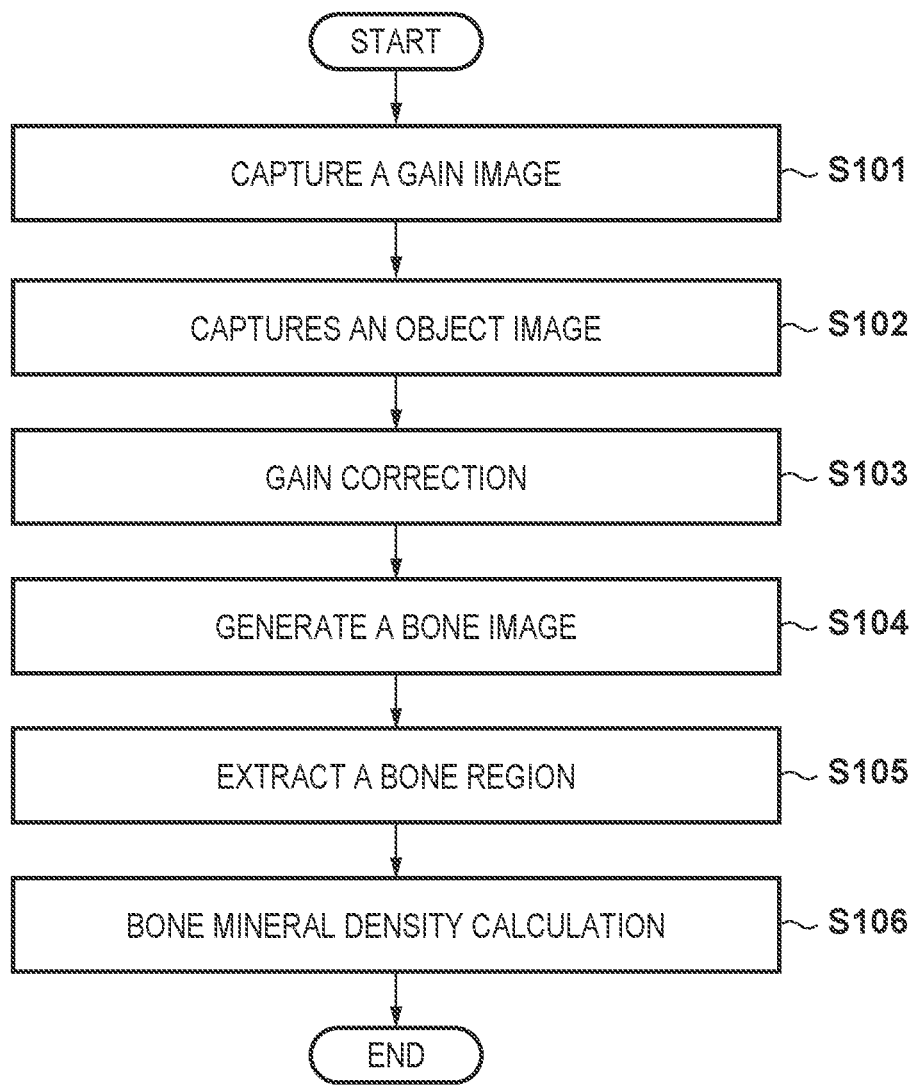

X-RAY IMAGE PROCESSING APPARATUS, X-RAY DIAGNOSIS APPARATUS, METHOD, AND STORAGE MEDIUM

BACKGROUND

Field of Disclosure

The embodiments disclosed in this specification and the accompanying drawings relate to an X-ray image processing apparatus, an X-ray diagnosis apparatus, a method, and a computer-readable storage medium.

Description of the Related Art

Conventionally, as a technique of generating an evaluation image for evaluating the state of a bone of an object, a DXA (Dual-energy X-ray Absorptiometry) method is known. In the DXA method, a bone image that discriminates a bone based on captured image data of an object corresponding to X-rays with two different types of energies is generated, and an index for evaluating the state of the bone of the object, such as a bone mineral density (BMD), is measured based on the generated bone image.

Since the bone mineral density is an index used to diagnose osteoporosis or determine the effect of a therapeutic agent, highly reproducible measurement is required for the diagnosis and determination. However, an X-ray generation apparatus cannot accurately implement the reproducibility of measurement of the index for evaluating the state of an object because of statistic output errors.

CITATION LIST

Patent Literature

Patent literature 1: Japanese Patent Laid-Open No. 2011-245117
Patent literature 2: Japanese Patent Laid-Open No. 2002-200071
Patent literature 3: Japanese Patent Laid-Open No. 2019-126581
Patent literature 4: Japanese Patent Laid-Open No. 2005-169068

There remains a need to improve the reproducibility of measurement of the index for evaluating the state of an object.

SUMMARY

According to one aspect of the present disclosure, there is provided an X-ray image processing apparatus comprising: a first obtaining unit configured to obtain a first X-ray image including an object; a second obtaining unit configured to obtain a first measured value associated with an X-ray condition of the first X-ray image, a second X-ray image that does not include the object, and a second measured value associated with an X-ray condition of the second X-ray image; a gain correction unit configured to correct the first X-ray image based on the first measured value, the second X-ray image, and the second measured value; and an image generation unit configured to generate an evaluation image for evaluating a state of the object based on a corrected image that is the first X-ray image corrected by the gain correction unit.

Further features of the present disclosure will become apparent from the following description of exemplary embodiments (with reference to the attached drawings).

BRIEF DESCRIPTION OF THE DRAWINGS

FIG. 2 is a flowchart showing a series of processes by a medical information processing system 1 according to the first embodiment.

DESCRIPTION OF THE EMBODIMENTS

Figure 1:
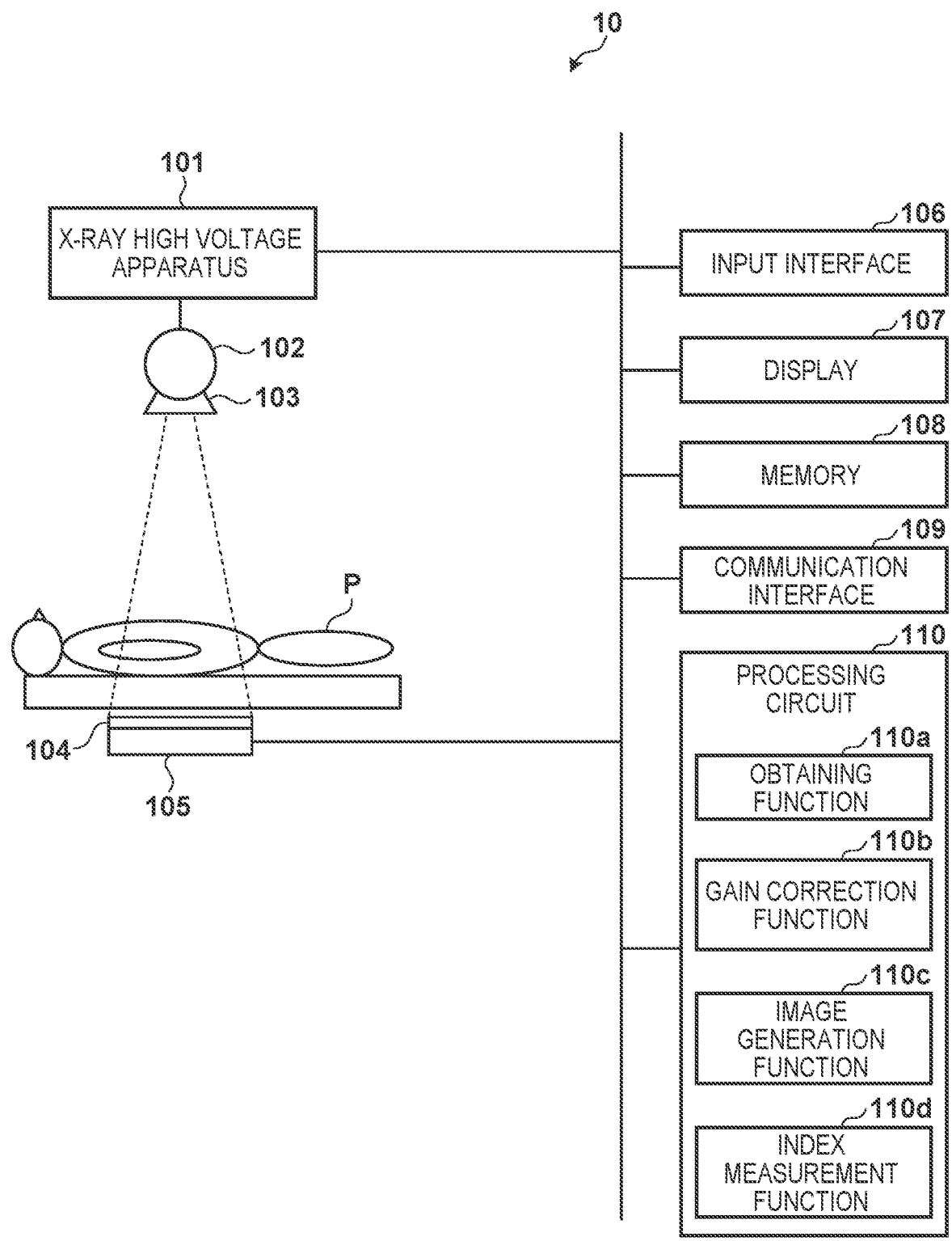
FIG. 1 is a block diagram showing an example of the configuration of an X-ray diagnosis apparatus according to the first embodiment.

Hereinafter, embodiments will be described in detail with reference to the attached drawings. Note, the following embodiments are not intended to limit the scope of the claimed subject matter. Multiple features are described in the embodiments, but limitation is not made to any particular embodiment that requires all such features, and multiple features of different embodiments may be combined or interchanged as appropriate. Furthermore, in the attached drawings, the same reference numerals are given to the same or similar configurations, and redundant description thereof is omitted.

First Embodiment

The configuration of an X-ray diagnosis apparatus 10 will be described with reference to FIG. 1. As shown in FIG. 1, the X-ray diagnosis apparatus 10 includes an X-ray high voltage apparatus 101, an X-ray tube 102, an X-ray aperture 103, a grid 104, an X-ray detector 105, an input interface 106, a display 107, a memory 108, a communication interface 109, and a processing circuit 110.

The X-ray high voltage apparatus 101 applies a high voltage to the X-ray tube 102. In addition, the X-ray high voltage apparatus 101 includes a voltage sensor and a current sensor and measures a tube voltage actually applied to the X-ray tube 102, a tube current supplied to the X-ray tube 102, and a pulse width. The X-ray tube 102 is a vacuum tube including a cathode with a filament, and an anode with a target. According to the high voltage applied from the X-ray high voltage apparatus 101, the X-ray tube 102 emits thermoelectrons from the filament to the target and makes the thermoelectrons collide the target, thereby generating X-rays.

The X-ray aperture 103 includes aperture blades made of an X-ray shielding material such as lead or tungsten, and an additional filter. The aperture blades narrow down the X-rays generated by the X-ray tube 102 and is provided to be slidable. The X-rays generated by the X-ray tube 102 are narrowed down by an opening formed by, for example, four aperture blades. In order to reduce the exposure dose of an object P and improve the quality of an X-ray image, the additional filter changes the radiation quality of transmitted X-rays by the material and thickness, reduces soft radiation components that are easily absorbed by the object P, and reduces high-energy components that cause a deterioration in the contrast of an X-ray image. In addition, the additional filter changes the dose and irradiation range of X-rays by the material, thickness, position, and the like and attenuates the X-rays so as to make the X-rays applied from the X-ray tube 102 to the object P have a predetermined distribution.

The grid 104 removes scattered rays (secondary X-rays) generated when the object P is irradiated with X-rays, and is detachably provided at a position between the X-ray detector 105 and a top plate on which the object P is placed. The grid 104 is made of, for example, an X-ray shielding material such as lead or tungsten, and formed into a grid shape. The grid 104 includes a single grid, a cross grid, a honeycomb grid, and the like. The single grid is a grid in which grid elements are formed parallelly in one direction. The cross grid is a grid in which grid elements are formed to cross each other. The honeycomb grid is a grid in which grid elements are formed in a honeycomb (hexagonal) pattern.

The X-ray detector 105 is formed by, for example, an FPD (Flat Panel Detector). The X-ray detector 105 detects X-rays emitted from the X-ray tube 102 and transmitted through the object P and the grid 104. The X-ray detector 105 supplies a detection signal corresponding to the detected X-rays to the processing circuit 110. Note that the X-ray detector 105 may have a structure formed by stacking two types of phosphors having different X-ray absorption sensitivities, such as CsI (cesium iodide) and GOS (gadolinium oxide sulfide). Thus, X-ray images (dual energies) of two types of energies can be collected by one X-ray irradiation. Also, the X-ray detector 105 can be any of indirect conversion type and direct conversion type.

The input interface 106 is formed by, for example, a mouse, a keyboard, a trackball, switches, buttons, a joystick, a touchpad on which an input operation is performed by touching the operation surface, a touch screen formed by integrating a display screen and a touchpad, a noncontact input circuit using an optical sensor, a voice input circuit, or the like. The input interface 106 accepts various kinds of input operations from a user, and supplies an electrical signal corresponding to the accepted input operation to the processing circuit 110.

The display 107 is formed by, for example, a display device such as a liquid crystal display or a CRT (Cathode Ray Tube) display. The display 107 displays various kinds of information supplied from the processing circuit 110.

The memory 108 is formed by a storage device, for example, a semiconductor memory element such as a RAM (Random Access Memory) or a flash memory, a hard disk, or an optical disk. The memory 108 stores various kinds of information supplied from the processing circuit 110. Also, the memory 108 stores programs to be executed by the processing circuit 110.

The communication interface 109 is formed by, for example, a network card, a network adapter, or the like. Under the control of the processing circuit 110, the communication interface 109 transmits/receives various kinds of information to/from an external apparatus connected via the network.

The processing circuit 110 is formed by an arithmetic processing device, for example, a CPU (Central Processing Unit) or an MPU (Micro-Processing unit). The processing circuit 110 controls the units of the X-ray diagnosis apparatus 10, thereby controlling the entire X-ray diagnosis apparatus 10.

In addition, the processing circuit 110 reads out and executes programs stored in the memory 108, thereby functioning as an obtaining function 110a, a gain correction function 110b, an image generation function 110c, and an index measurement function 110d. The obtaining function 110a is an example of a first obtaining unit and a second obtaining unit. The gain correction function 110b is an example of a gain correction unit. The image generation function 110c is an example of an image generation unit. The index measurement function 110d is an example of an index measurement unit.

The X-ray diagnosis apparatus 10 configured as described above generates, for example, a bone image as an evaluation image for evaluating the state of the object P. Based on the generated bone image, the X-ray diagnosis apparatus 10 measures an index for evaluating the state of a bone of the object P, such as a bone mineral density (BMD).

Here, X-rays emitted from the X-ray tube 102 have statistic output errors. For example, even if the same X-ray conditions are set, it is difficult to accurately implement the output reproducibility of the X-ray high voltage apparatus 101 (control limit of the X-ray high voltage apparatus 101). The X-ray diagnosis apparatus 10 performs processing of reducing output errors that statistically occur, thereby improving the reproducibility of measurement of the index for evaluating the state of the object P.

The processing executed by the X-ray diagnosis apparatus 10 will be described below with reference to FIG. 2. The obtaining function 110a captures a gain image that is an X-ray image without the object P (step S101). For example, in a state in which the object P is not arranged on the X-ray path between the X-ray tube 102 and the X-ray detector 105, the obtaining function 110a captures a high-energy gain image ($I_{HG}$) of 140 kV and a low-energy gain image ($I_{LG}$) of 80 kV. The obtaining function 110a stores the captured energy gain images in the memory 108.

Also, the obtaining function 110a stores, in the memory 108, measured values associated with X-ray conditions at the time of gain image capturing. More specifically, when capturing each energy gain image, the X-ray high voltage apparatus 101 measures a tube voltage ($V_{HG}$) actually applied to the X-ray tube 102, a tube current ($A_{HG}$) actually supplied to the X-ray tube 102, and a pulse width ($T_{HG}$). The obtaining function 110a obtains the results measured by the X-ray high voltage apparatus 101 and stores these in the memory 108.

In addition, the obtaining function 110a captures an object image that is an X-ray image including the object P (step S102). For example, in a state in which the object P is arranged on the X-ray path between the X-ray tube 102 and the X-ray detector 105, the obtaining function 110a captures a high-energy object image (a high-energy image $I_H$ shown in FIG. 3A) of 140 kV and a low-energy object image (a low-energy image $I_L$ shown in FIG. 3B) of 80 kV. The obtaining function 110a stores the captured object images in the memory 108. Note that the object P is a patient or a phantom for calibration.

Also, the obtaining function 110a stores, in the memory 108, measured values associated with X-ray conditions at the time of object image capturing. More specifically, when capturing each object image, the X-ray high voltage apparatus 101 measures the tube voltage ($V_{HG}$) actually applied to the X-ray tube 102, the tube current ($A_{HG}$) actually supplied to the X-ray tube 102, and the pulse width ($T_{HG}$). The obtaining function 110a obtains the results measured by the X-ray high voltage apparatus 101 and stores these in the memory 108.

Note that if the X-ray detector 105 has a structure formed by stacking two types of phosphors having different X-ray absorption sensitivities, the obtaining function 110a can collect the high- and low-energy gain images and the high- and low-energy object images by one X-ray irradiation. Note that when performing imaging by the stacked type detector, it is preferable that the additional filter of the X-ray detector 105 is not provided. This is because if the additional filter is provided, room for beam hardening becomes small, and the energy separation capability degrades.

Step S101 and step S102 are performed in an arbitrary order. Step S101 can appropriately be omitted. For example, gain image capturing may be performed periodically. That is, the obtaining function 110a periodically captures the gain images and stores these in the memory 108. Instead of executing step S101, the obtaining function 110a may appropriately obtain gain images stored in the memory 108.

Figure 3A:
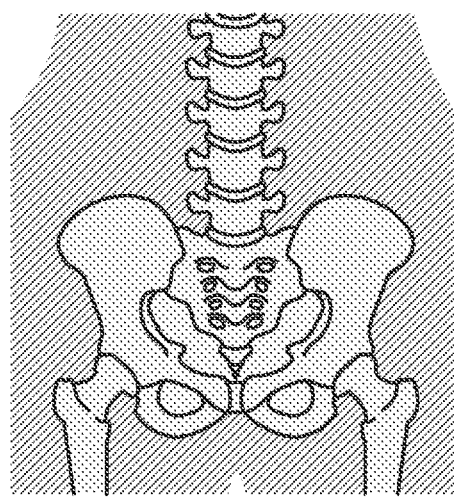
FIG. 3A is a view showing an example of a high-energy object image according to the first embodiment.
Figure 3B:
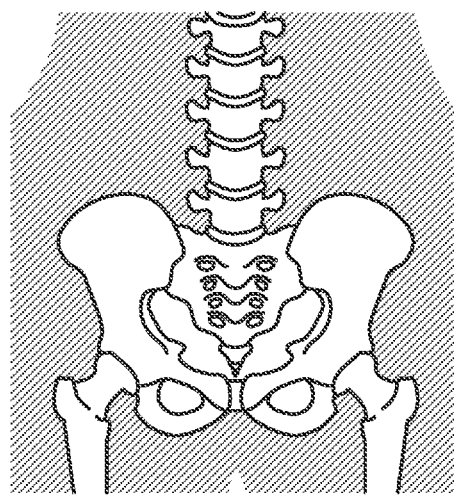
FIG. 3B is a view showing an example of a low-energy object image according to the first embodiment.

For example, the high-energy image $I_H$ shown in FIG. 3A and the low-energy image $I_L$ shown in FIG. 3B are expressed by $$I_H = I_{H0} \exp(-\mu_{HA}\sigma_A - \mu_{HB}\sigma_B) \quad (1)$$

$$I_L = I_{L0} \exp(-\mu_{LA}\sigma_A - \mu_{LB}\sigma_B) \quad (2)$$

$I_{H0}$ and $I_{L0}$ are a high-energy image and a low-energy image obtained if the imaging in step S102 is performed in the state without the object P, and these are different from the energy gain images ($I_{HG}$ and $I_{LG}$) captured in step S101. In addition, $\mu_{HA}$ and $\mu_{LA}$ are mass attenuation coefficients for a soft tissue at a high energy and a low energy, respectively. Also, $\mu_{HB}$ and $\mu_{LB}$ are mass attenuation coefficients for a bone at a high energy and a low energy, respectively. Also, σA is the density of the soft tissue, and GB is the bone mineral density. The mass attenuation coefficient is expressed using, for example, "cm²/g" as a unit. The density is expressed using, for example, "g/cm²" as a unit.

If $I_{HG}$ is the high-energy gain image, and $I_{LG}$ is the low-energy gain image, the high-energy image and the low-energy image after gain correction are expressed by $$\frac{I_H}{I_{HG}} = \frac{I_{H0}}{I_{HG}} \exp(-\mu_{HA}\sigma_A - \mu_{HB}\sigma_B) \quad (3)$$

$$\frac{I_L}{I_{LG}} = \frac{I_{L0}}{I_{LG}} \exp(-\mu_{LA}\sigma_A - \mu_{LB}\sigma_B) \quad (4)$$

Here, if the X-ray conditions set in steps S101 and S102 equal, imaging doses equal theoretically. Hence, "$I_{H0}=I_{HG}$", and "$I_{L0}=I_{LG}$". However, because of the control limit of the X-ray high voltage apparatus 101, statistic errors are generated in the measured values associated with the X-ray conditions between step S101 and step S102. Hence, "$I_{H0} \neq I_{HG}$", and "$I_{L0} \neq I_{LG}$".

In general, the imaging dose is proportional to a tube current A and a pulse width T, which are actually measured. In addition, a tube voltage V and the imaging dose hold a nonlinear relationship. Hence, if the relationship is defined as a function F(V), and equations (3) and (4) are corrected by the measured values, we obtain $$\frac{I_H A_{HG} T_{HG}}{I_{HG} A_{B0} T_{H0}} = \quad (5)$$

$$\frac{I_{H0} A_{HG} T_{HG} F(V_{HG})}{I_{HG} A_{H0} T_{H0} F(V_{H0})} \exp(-\mu_{HA}\sigma_A - \mu_{HB}\sigma_B) = \exp(-\mu_{HA}\sigma_A - \mu_{HB}\sigma_B)$$

$$\frac{I_L A_{LG} T_{LG}}{I_{LG} A_{L0} T_{H0}} = \quad (6)$$

$$\frac{I_{L0} A_{LG} T_{LG} F(V_{LG})}{I_{LG} A_{L0} T_{L0} F(V_{L0})} \exp(-\mu_{LA}\sigma_A - \mu_{LB}\sigma_B) = \exp(-\mu_{LA}\sigma_A - \mu_{LB}\sigma_B)$$

Note that the subscript "HG" means capturing of the high-energy gain image in step S101. The subscript "LG" means capturing of the low-energy gain image in step S101. The subscript "H0" means capturing of the high-energy object image in step S102. The subscript "L0" means capturing of the low-energy object image in step S102.

The gain correction function 110b executes gain correction for the object images of high- and low-energies by equations (5) and (6) (step S103). That is, the gain correction function 110b performs gain correction of the object images based on the measured values associated with the X-ray conditions of the object images, the gain images, and the measured values associated with the X-ray conditions of the gain images.

More specifically, the gain correction function 110b performs gain correction of the high-energy image $I_H$ based on the measured values ($A_{H0}$, $T_{H0}$, and $V_{H0}$) associated with the X-ray conditions of the high-energy image $I_H$, the high-energy gain image $I_{HG}$, and the measured values ($A_{HG}$, $T_{HG}$, and $V_{HG}$) associated with the X-ray conditions of the high-energy gain image $I_{HG}$.

The gain correction function 110b performs gain correction of the low-energy image $I_L$ based on the measured values ($A_{L0}$, $T_{L0}$, and $V_{L0}$) associated with the X-ray conditions of the low-energy image $I_L$, the low-energy gain image $I_{LG}$, and the measured values ($A_{LG}$, $T_{LG}$, and $V_{LG}$) associated with the X-ray conditions of the low-energy gain image $I_{LG}$.

Note that the function F(V) in equations (5) and (6) depends on the entire system including the X-ray high voltage apparatus 101, the X-ray tube 102, the X-ray aperture 103, and the grid 104. It is therefore preferable that the tube voltage dependence of a pixel value is measured in advance using the X-ray detector 105, and the function F(V) is approximated by a lookup table or a polynomial function. Alternatively, the relationship between the measured tube current A, pulse width T, and tube voltage V and a pixel value measured using the X-ray detector 105 may be defined as the general function F(V), and the function may be approximated by a lookup table or a polynomial function, thereby performing the above-described gain correction.

Thus, the gain correction function 110b can reduce the difference in the X-ray sensitivity between detection elements in the X-ray detector 105 or statistically generated output errors in the X-ray tube 102 and accurately cancel the bias of the dose and distribution of X-rays emitted from the X-ray tube 102.

Figure 3C:
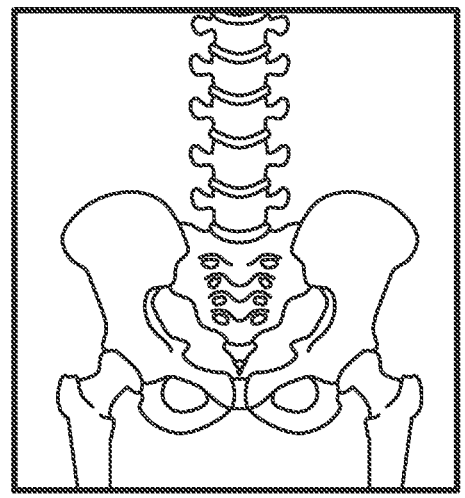
FIG. 3C is a view showing an example of a bone image according to the first embodiment.

The image generation function 110c calculates the logarithmic difference between the high-energy image and the low-energy image, which have undergone the gain correction in step S103, thereby generating a bone image IB shown in FIG. 3C (step S104). The bone image IB is an example of an image representing the target region of the object P and an evaluation image for evaluating the state of the object P.

Figure 5A:
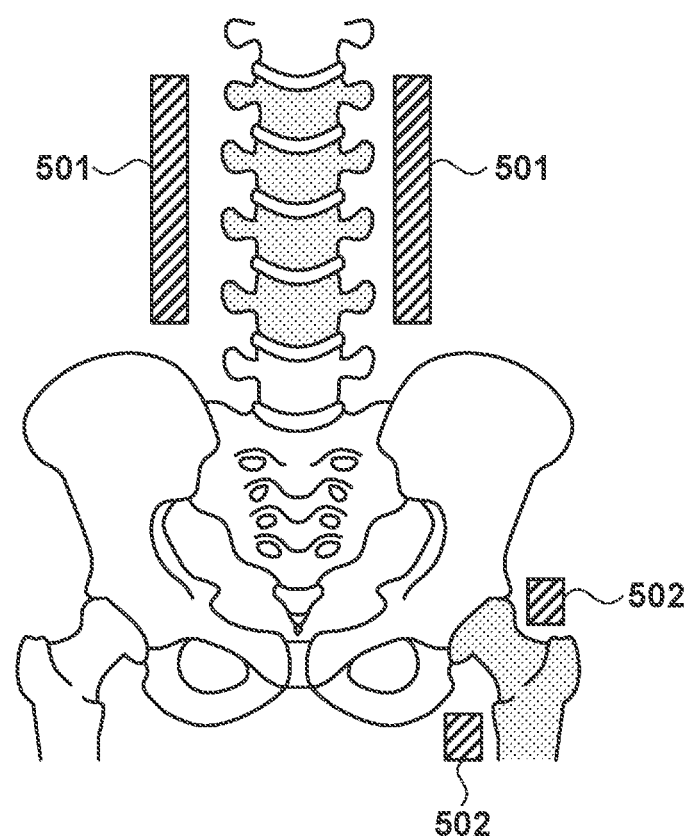
FIG. 5A is a view for explaining bone mineral density calculation processing according to the first embodiment.

More specifically, the image generation function 110c performs logarithmic transformation for equations (5) and (6). That is, the image generation function 110c performs logarithmic transformation for the object images of the energies after gain correction. The image generation function 110c multiplies one of the object images of the energies after logarithmic transformation by "$\mu_{LA}/\mu_{HA}$" and subtracts the result from the other object image. Thus, the image generation function 110c generates the bone image IB represented by equation (7) and shown in FIG. 3C. Note that "$\mu_{LA}/\mu_{HA}$" is an example of a predetermined coefficient, and is set such that pixel values of a portion (for example, a portion 501 or 502 in FIG. 5A) made of only a soft tissue part in the object P become "0" when creating the bone image IB shown in FIG. 3C.

$$I_B = \left(\mu_{LB} - \frac{\mu_{LA}}{\mu_{HA}}\mu_{HB}\right)\sigma_B \quad (7)$$

Figure 4:
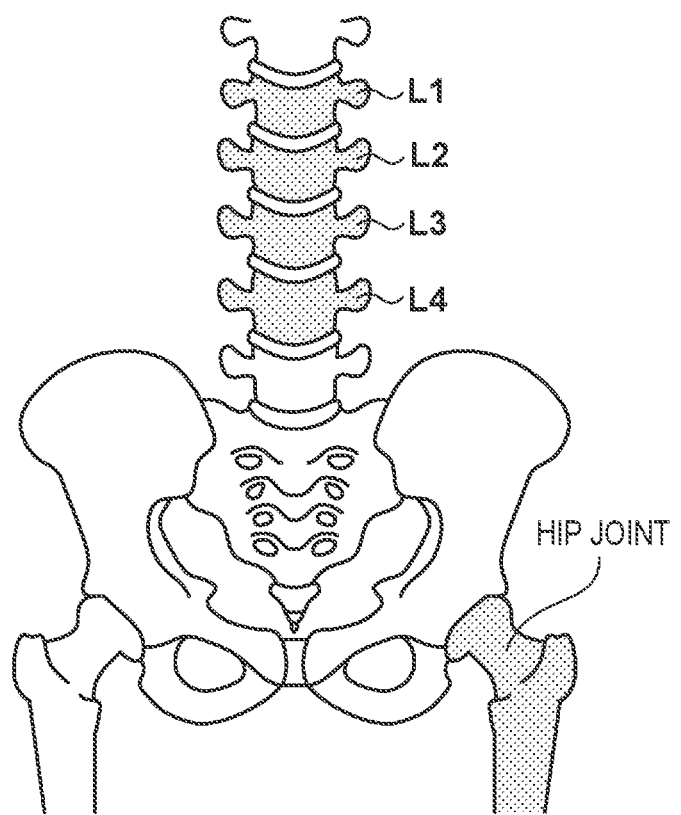
FIG. 4 is a view showing an example of region extraction processing according to the first embodiment.

The index measurement function 110d extracts a bone region used to measure an index for evaluating the state of the bone of the object P, such as a bone mineral density (BMD), from the bone image IB shown in FIG. 3C (step S105). For example, the index measurement function 110d extracts the bone region by accepting, from the user, an operation of selecting the bone region via the input interface 106. FIG. 4 shows an example of extraction of the bone region. FIG. 4 shows a case where L1 to L4 are selected as analysis regions of the spine, and a hip joint is selected as an analysis region of a femur.

Also, the index measurement function 110d may automatically extract the bone region by segmentation processing. As the method of segmentation, a water-shed method, graph cut, GrabCut, or the like can be used. The index measurement function 110d may automatically extract the bone region by, for example, a machine learning technique such as Unet or PSPnet. If a bone region is extracted by a user operation, the extracted bone region may be different between users. Even if the user is the same, the extracted bone region may change every time the operation is performed. If the index measurement function 110d automatically extracts the bone region, reproducibility of bone region extraction or bone mineral density calculation processing to be described later can be improved.

Figure 5B:
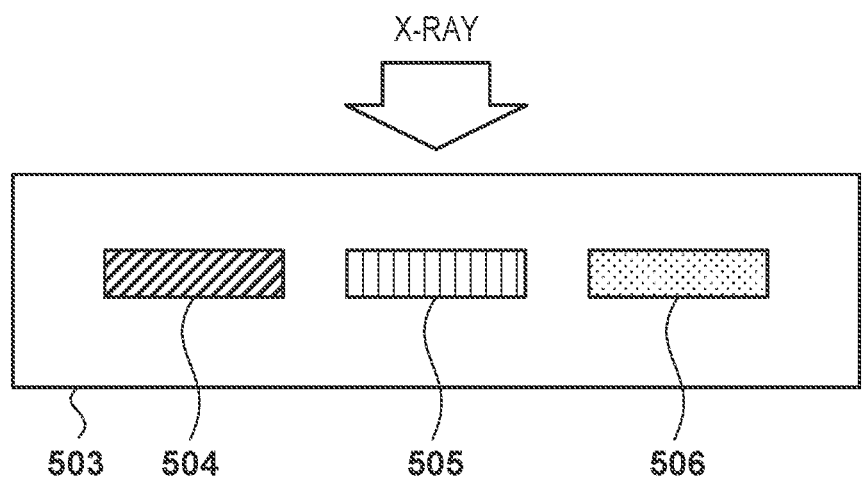
FIG. 5B is a view for explaining bone mineral density calculation processing according to the first embodiment.
Figure 5C:
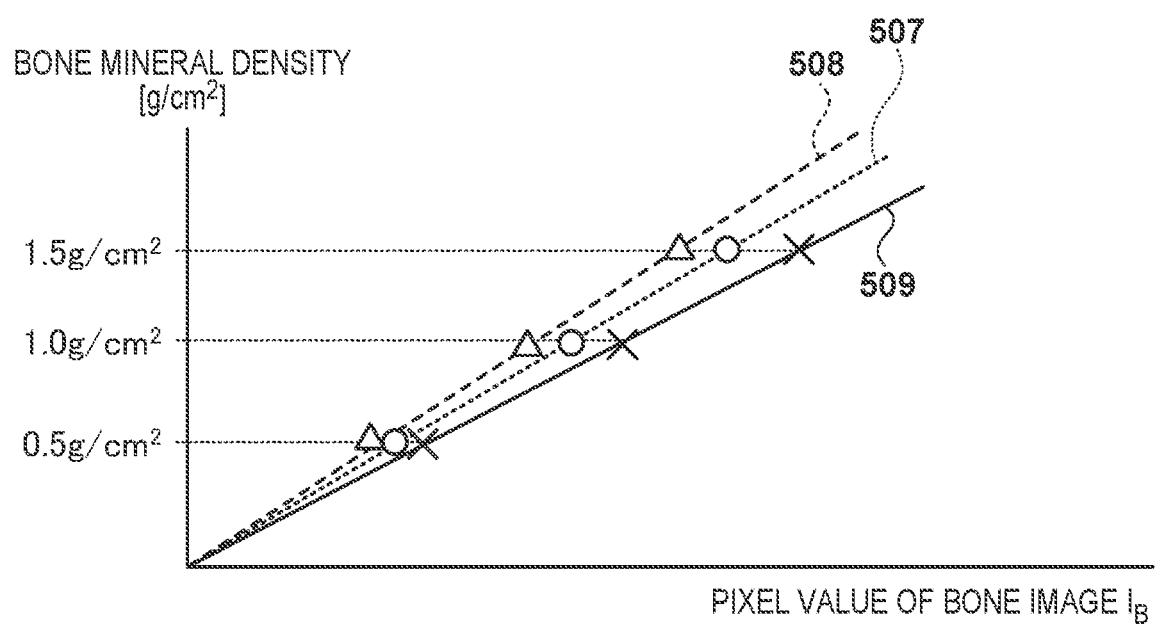
FIG. 5C is a view for explaining bone mineral density calculation processing according to the first embodiment.

The index measurement function 110d calculates the bone mineral density in each bone region extracted in step S105 (step S106). More specifically, using a calibration phantom shown in FIG. 5B, the index measurement function 110d converts a pixel value of the bone image IB into a bone mineral density "$g/cm^2$". Note that in FIG. 5B, simulated bones 504, 505, and 506 are buried in an acrylic resin 503. The bone mineral densities of the simulated bones 504, 505, and 506 are "0.5 $g/cm^2$", "1.0 $g/cm^2$", and "1.5 $g/cm^2$", respectively. If the calibration phantom is captured under the same conditions as the object P, and a bone image represented by equation (7) is generated, a calibration curve 507 representing the relationship between the bone mineral density and the pixel value shown in FIG. 5C is obtained from the bone image. A pixel value of the bone image IB of the object P can be converted into the bone mineral density "$g/cm^2$" based on the calibration curve.

In addition, the mass attenuation coefficient μ depends on the energy of X-rays. As is apparent from equation (7), the calibration curve 507 changes depending on variations in the tube voltage in high-energy imaging and the tube voltage in low-energy imaging. Hence, calibration curves, like calibration curves 508 and 509, according to a plurality of tube voltages may be obtained in advance and approximated by a lookup table or a polynomial function. By applying a calibration curve according to the measured value of the tube voltage, the bone mineral density can be calculated more accurately. That is, the index measurement function 110d obtains a calibration curve according to the tube voltage associated with the X-ray conditions of a first X-ray image including the object and measures the index (bone mineral density) based on the obtained calibration curve and the evaluation image, thereby improving the measurement accuracy of the index.

The result of bone mineral density calculation processing by the index measurement function 110d can be displayed on the display 107. For example, the display 107 displays the value of the calculated bone mineral density "$g/cm^2$". Alternatively, the X-ray diagnosis apparatus 10 may transmit the result of bone mineral density calculation processing to another apparatus via the network NW. In this case, the result of bone mineral density calculation processing is displayed on the other apparatus and provided to a user such as a doctor.

As described above, according to the first embodiment, the obtaining function 110a obtains the object image (first X-ray image) that is an X-ray image including the object P. Also, the obtaining function 110a obtains measured values (first measured values) associated with the X-ray conditions of the object image, a gain image (second X-ray image) that is an X-ray image without the object P, and measured values (second measured values) associated with the X-ray conditions of the gain image. The gain correction function 110b corrects the first X-ray image based on the first measured values, the second X-ray image, and the second measured values. The image generation function 110c generates an evaluation image for evaluating the state of the object P based on a corrected image that is the first X-ray image corrected by the gain correction function 110b. Thus, the X-ray diagnosis apparatus 10 according to the first embodiment can improve the accuracy of gain correction by reducing the influence of output errors of X-rays and improve the reproducibility of measurement of the index (for example, the bone mineral density) for evaluating the state of the object.

Figure 6:
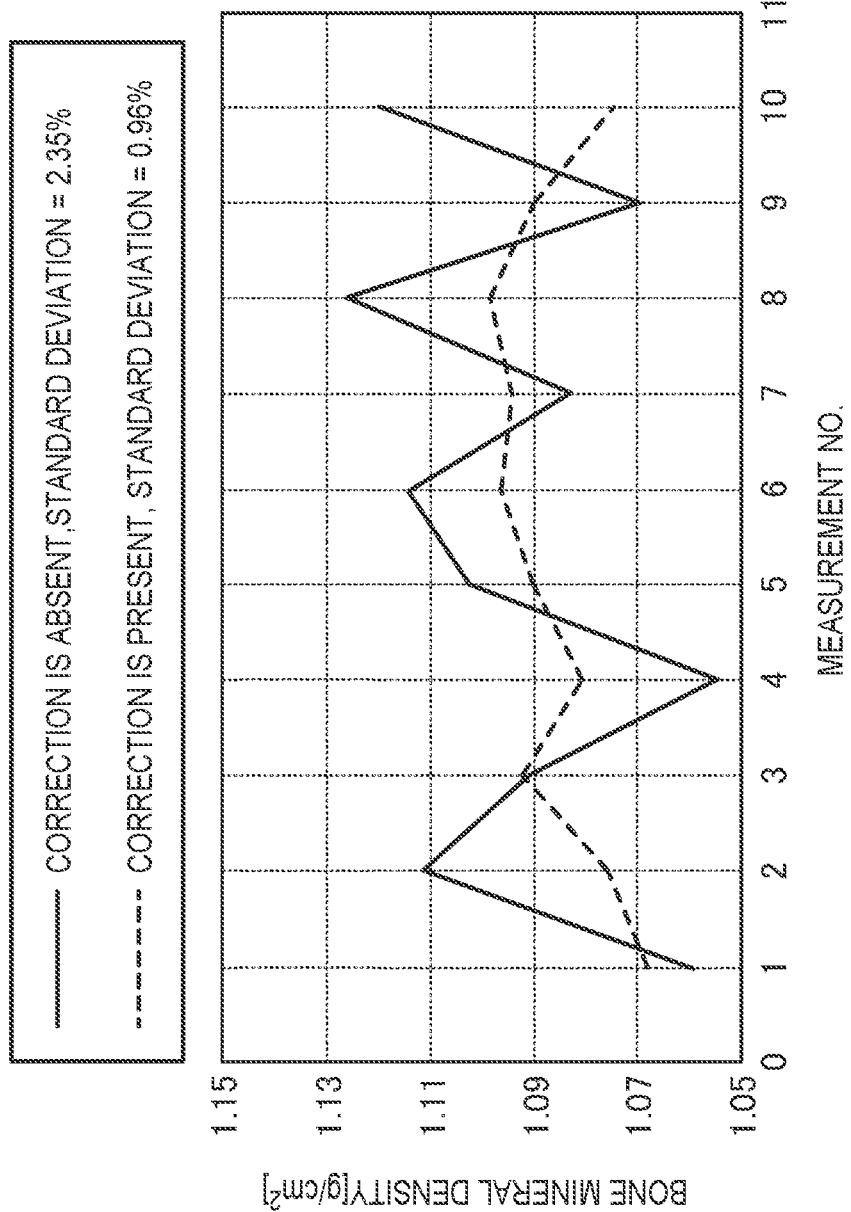
FIG. 6 is a view showing a reproducibility evaluation result according to the first embodiment.

FIG. 6 shows the reproducibility evaluation result of the bone mineral density calculated by the series of processes in FIG. 2. In this evaluation, the high-energy tube voltage was "140 kV", the low-energy tube voltage was "80 kV", and a copper plate having a thickness of "0.5 mm" was used as the additional filter of the X-ray aperture 103. Also, in this evaluation, a geometric phantom as in FIG. 5B was used as the measurement target. As shown in FIG. 6, if correction in step S103 is absent, "standard deviation=2.35%", and if correction in step S103 is present, reproducibility of "standard deviation=2.35%" can be implemented.

Figure 7:
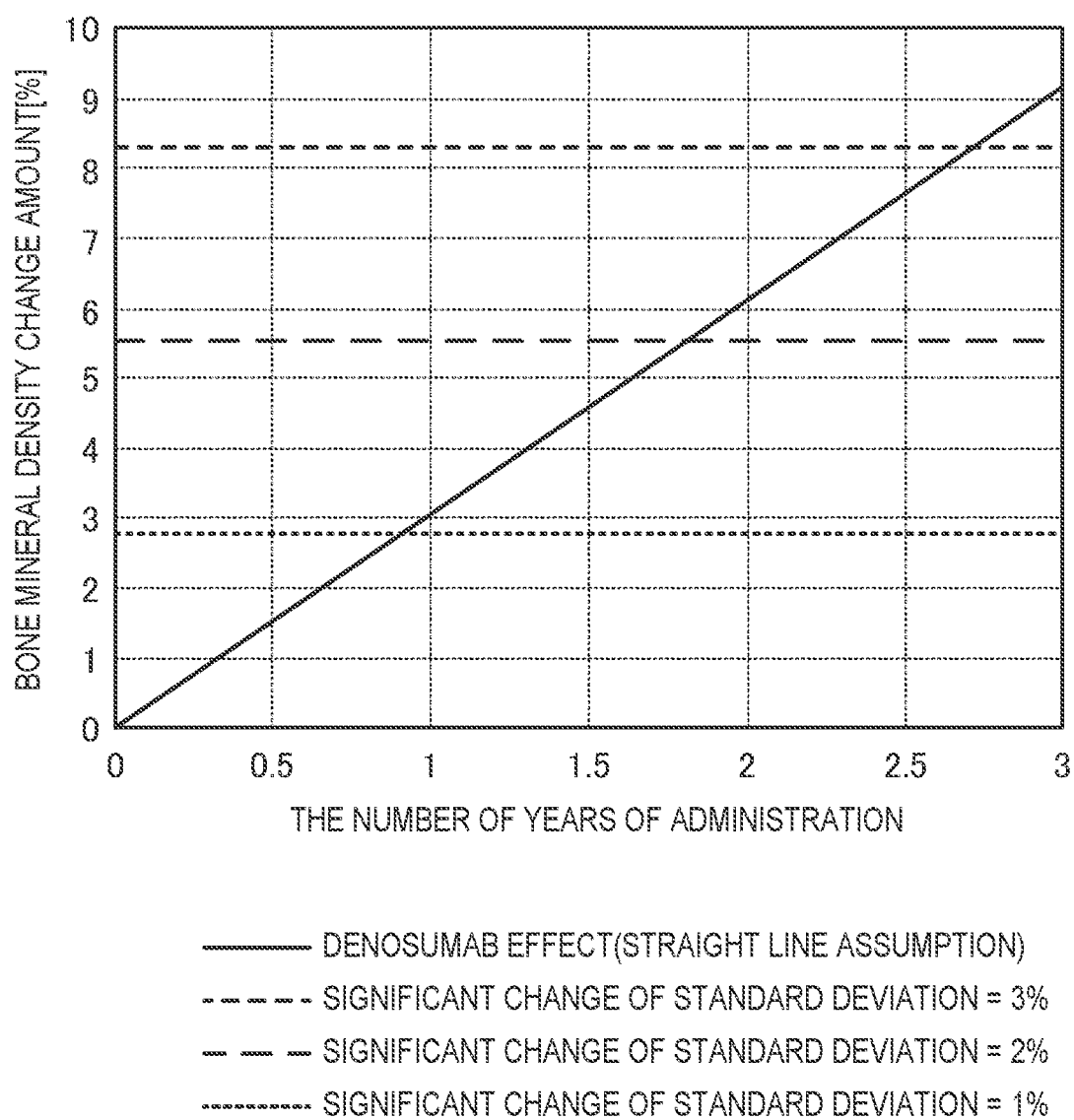
FIG. 7 is a view showing the linear approximation result of the number of years of administration and the bone mineral density change amount according to the first embodiment.

FIG. 7 shows the linear approximation result of the number of years of administration and the bone mineral density change amount using denosumab that is a therapeutic agent of osteoporosis as an example. According to FIG. 7, if the reproducibility of bone mineral density measurement is "1%", a significant change is observed in "0.9 years". If the reproducibility is "2%", "1.8 years" are taken until a significant change is observed, and if the reproducibility is "3%", "2.7 years" are taken until a significant change is observed, as can be seen. As described above, if the accuracy of bone mineral density calculation processing is improved, and the reproducibility is raised, the medicine effect can be determined earlier.

Note that in this embodiment, an example in which gain correction is performed for X-ray images of two types of energies has been described. The processing can similarly be performed even in a case where gain correction is performed for X-ray images of one or three or more types of energies.

Also, in this embodiment, an example in which the measured values of the tube voltage, the tube current, and the pulse width are used has been described. However, a combination of two of the tube voltage, the tube current, and the pulse width, or only one of the tube voltage, the tube current, and the pulse width may be used.

Second Embodiment

In the above-described embodiment, a case where the tube current at the time of obtaining the gain image and the object image is measured, and at least one of the gain image and the object image is corrected based on the measurement result has been described.

Here, the measured value of the tube current may temporally vary in one pulse due to a transient phenomenon. Additionally, in the transient phenomenon, overshoot is an apparent tube current change in the measurement and does not exist in fact and is also affected by the state of the apparatus. From these circumstances, the influence of the transient phenomenon cannot completely be eliminated depending on the measured value at one point of time, the average value of measured values at a plurality of points of time, or an integrated value in a predetermined section, and an appropriate measured value of the tube current cannot necessarily be obtained.

Hence, in steps S101 and S102 shown in FIG. 2, the tube current may be measured time-serially. That is, the first measured value and the second measured values described above may be waveform data of the tube current. A gain correction function 110b analyzes the waveform data of the tube current and estimates the value of the tube current to be used in gain correction of step S103. This allows the gain correction function 110b to obtain an appropriate tube current value to be used in gain correction in consideration of the influence of the transient phenomenon. Note that to estimate the measured value of the tube current, for example, a method using simulations or a method using a learned model by machine learning can be used.

Also, an obtaining function 110a may obtain the results of waveform analysis and tube current estimation in real time in parallel to X-ray irradiation, and perform AEC (Auto Exposure Control) based on the estimated value of the tube current. This can raise the reproducibility of X-ray output and further improve the accuracy of analysis processing based on an X-ray image.

Third Embodiment

Another method for eliminating the influence of the transient phenomenon described in the second embodiment will be described. For example, in gain image capturing of step S101, an X-ray diagnosis apparatus 10 changes the set value of the tube current and collects a plurality of gain images. The plurality of gain images are stored in, for example, a memory 108. Note that a gain image captured in advance for each set value of the tube current will also be referred to as a preliminary gain image.

After that, if an object image is captured in step S102, the gain correction function 110b selects and obtains an appropriate one of the plurality of gain images captured in advance. More specifically, the gain correction function 110b selects a gain image closest to the measured value of the tube current at the time of imaging the object image from the plurality of gain images of different tube current set values, and uses the gain image in gain correction of step S103. Alternatively, the gain correction function 110b may perform interpolation processing using the plurality of gain images of different tube current set values, generate a gain image corresponding to the measured value of the tube current at the time of imaging the object image, and use the gain image in gain correction of step S103.

Alternatively, the gain correction function 110b may measure the tube current time-serially and select an appropriate gain image based on the degree of matching of waveforms. That is, the gain correction function 110b may compare the waveform of the tube current at the time of capturing each of the plurality of gain images with the waveform of the tube current at the time of capturing the object image, select a gain image with the closest waveform, and use it in gain correction of step S103. In this case, a plurality of gain images may be collected in correspondence with each set value of the tube current.

According to the third embodiment, it is possible to perform gain correction processing in consideration of the transient phenomenon of the tube current by a simpler implementation. Also, when selecting a gain image based on the degree of matching of waveforms, even if the reproducibility of the tube current waveform is low, appropriate gain correction can be performed. It is also possible to improve the accuracy of analysis processing based on the X-ray image.

Fourth Embodiment

Still another method for eliminating the influence of the transient phenomenon described in the second and third embodiments will be described. A gain correction function 110b calculates the measured value of the tube current value based on the data of an area dosimeter, the measured value of the tube voltage, and the measured value of the pulse width.

That is, when capturing a gain image and an object image, an X-ray diagnosis apparatus 10 measures a dose of irradiation by an area dosimeter. The irradiation dose can be expressed by a function according to the tube current, the tube voltage, and the pulse width. The gain correction function 110b can calculate backwards the measured value of the tube current value based on the data of the area dosimeter, the measured value of the tube voltage, and the measured value of the pulse width. According to this method as well, it is possible to perform gain correction while eliminating the influence of the transient phenomenon of the tube current and improve the accuracy of analysis processing based on the X-ray image.

Fifth Embodiment

In the above-described embodiments, the bone image shown in FIG. 3C has been described as an example of the evaluation image for evaluating the state of the object P.

However, the embodiment is not limited to this, and various modifications can be made for the target region of the evaluation image generated by an image generation function 110c.

For example, an X-ray diagnosis apparatus 10 may be a mammography apparatus including a press plate configured to press the breast of an object P, and may generate a breast image for evaluating the state of the breast of the object P. In this case as well, as in the above-described embodiments, an obtaining function 110a obtains an object image (first X-ray image) that is an X-ray image including the object P. The X-ray image is an MLO (Mediolateral-Oblique) image or a CC (Cranio-Caudal) image. Also, as in the above-described embodiments, the obtaining function 110a obtains measured values (first measured values) associated with the X-ray conditions of the object image, a gain image (second X-ray image) that is an X-ray image without the object P, and measured values (second measured values) associated with the X-ray conditions of the gain image. A gain correction function 110b corrects the first X-ray image based on the first measured values, the second X-ray image, and the second measured values, as in the above-described embodiments. The image generation function 110c generates an evaluation image (here, a breast image) for evaluating the state of the mammary gland of the object P based on a corrected image that is the first X-ray image corrected by the gain correction function 110b.

An index measurement function 110d executes analysis processing based on the mammary gland image and calculates a breast density (BD). For example, the index measurement function 110d sets, for the mammary gland image, a first region corresponding to the breast and a second region where a mammary gland exists, and divides the area of the second region by the area of the first region, thereby calculating the breast density.

In the above-described embodiments, steps S103 to S106 in FIG. 2 are executed in the X-ray diagnosis apparatus 10. However, these processes may be performed in an apparatus different from the X-ray diagnosis apparatus 10. For example, the processes of steps S103 to S106 may be performed by an X-ray image processing apparatus 30 shown in FIG. 8.

Figure 8:
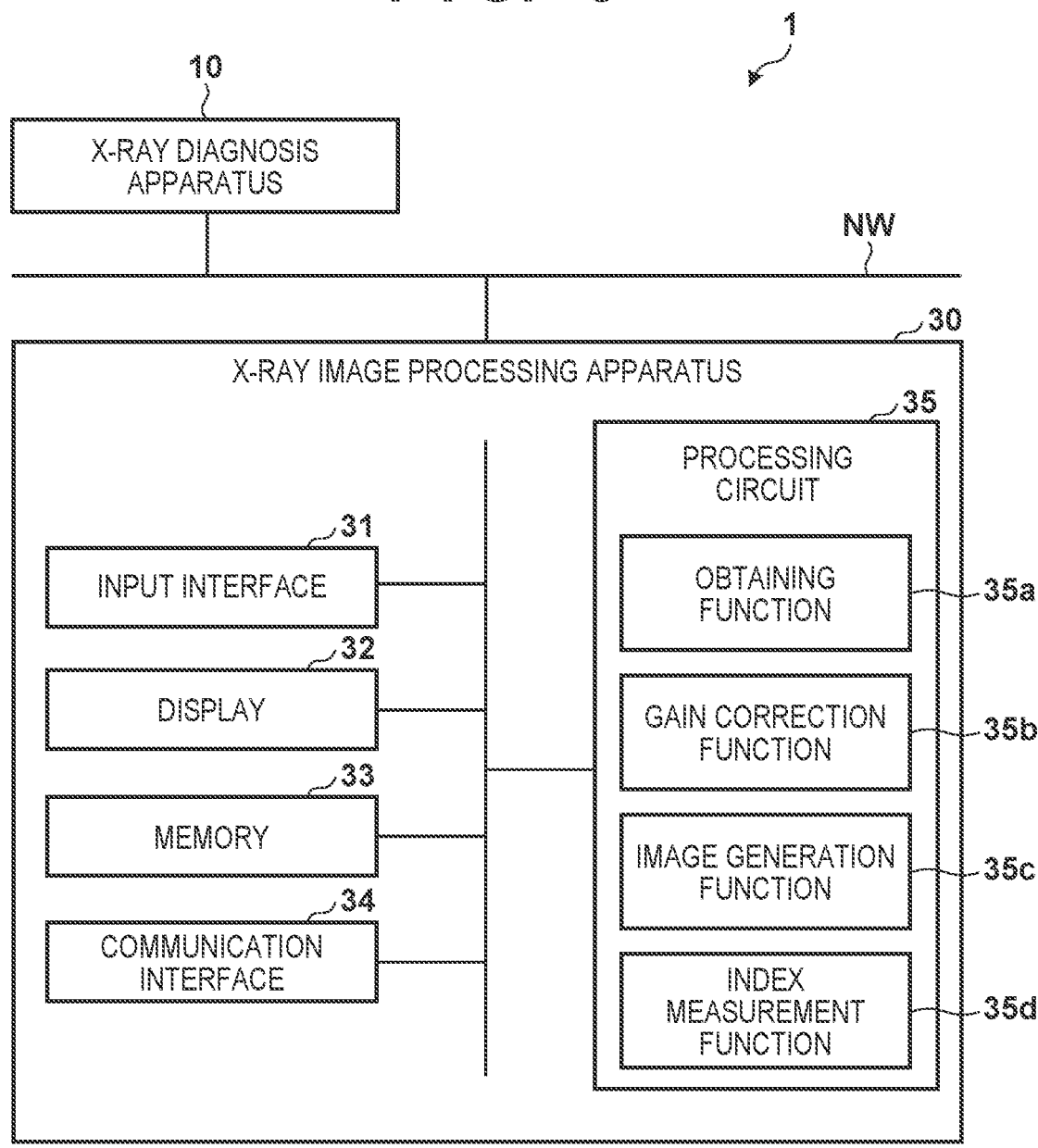
FIG. 8 is a block diagram showing an example of the configuration of an X-ray diagnosis apparatus according to the fifth embodiment.

In a medical information processing system 1 shown in FIG. 8, the X-ray diagnosis apparatus 10 and the X-ray image processing apparatus 30 are connected to each other via a network NW. The X-ray diagnosis apparatus 10 obtains the first X-ray image, the first measured values, the second X-ray image, and the second measured values described above and transmits these to the X-ray image processing apparatus 30 via the network NW.

Note that the transmission of various kinds of information from the X-ray diagnosis apparatus 10 to the X-ray image processing apparatus 30 may be performed via another apparatus. As an example, the X-ray diagnosis apparatus 10 transmits the obtained X-ray images and measured values to an image saving apparatus such as a PACS (Picture Archiving and Communication System) and causes it to store these. In this case, the X-ray image processing apparatus 30 can obtain the X-ray images and the measured values from the image saving apparatus.

For example, as shown in FIG. 8, the X-ray image processing apparatus 30 includes an input interface 31, a display 32, a memory 33, a communication interface 34, and a processing circuit 35.

The input interface 31 can be configured, like the above-described input interface 106. For example, the input interface 31 accepts various kinds of input operations from the user of the X-ray image processing apparatus 30, converts the accepted input operation into an electrical signal, and outputs it to the processing circuit 35.

The display 32 can be configured, like the above-described display 107. For example, under the control of the processing circuit 35, the display 32 displays an X-ray image, a processing result of the processing circuit 35, and a GUI configured to accept various kinds of instructions and settings from the user.

The memory 33 can be configured, like the above-described memory 108. For example, the memory 33 stores an X-ray image, a processing result of the processing circuit 35, a program to be executed by the processing circuit 35, and the like.

The communication interface 34 can be configured, like the above-described communication interface 109. For example, the communication interface 34 is connected to the network NW, thereby performing information communication between the X-ray diagnosis apparatus 10 and the X-ray image processing apparatus 30.

The processing circuit 35 is formed by an arithmetic processing device, for example, a CPU or an MPU, and controls the units of the X-ray image processing apparatus 30, thereby controlling the entire X-ray image processing apparatus 30. In addition, the processing circuit 35 reads out and executes programs stored in the memory 33, thereby functioning as an obtaining function 35a, a gain correction function 35b, an image generation function 35c, and an index measurement function 35d.

The obtaining function 35a is an example of a first obtaining unit and a second obtaining unit. The obtaining function 35a obtains various kinds of information such as the first X-ray image, the first measured values, the second X-ray image, and the second measured values described above from the X-ray diagnosis apparatus 10 via the network NW.

The gain correction function 35b is the same function as the above-described gain correction function 110b, and corrects the first X-ray image based on the first measured values, the second X-ray image, and the second measured values, thereby obtaining the corrected image of the first X-ray image. The image generation function 35c is the same function as the above-described image generation function 110c, and generates an evaluation image for evaluating the state of the object P based on the corrected image. The index measurement function 35d is the same function as the above-described index measurement function 110d, and measures an index for evaluating the state of the object P based on the evaluation image generated by the image generation function 35c.

In the X-ray image processing apparatus 30 shown in FIG. 8, each processing function is stored, in the memory 33, in the form of a program executable by a computer. The processing circuit 35 is a processor that reads out a program from the memory 33 and executes it, thereby implementing a function corresponding to the program. In other words, the processing circuit 35 in a state in which a program is read out has a function corresponding to the readout program.

Note that in FIG. 8, the obtaining function 35a, the gain correction function 35b, the image generation function 35c, and the index measurement function 35d are implemented by the single processing circuit 35. The processing circuit 35 may be formed by combining a plurality of independent processors, and each processor may execute a program to implement a function. Also, the processing functions of the processing circuit 35 may be implemented by appropriately distributing or integrating these to a single or a plurality of processing circuits.

Also, the processing circuit 35 may implement the functions using the processor of an external apparatus connected via the network NW. For example, the processing circuit 35 reads out a program corresponding to each function from the memory 33 and executes it, and uses a server group (cloud) connected to the X-ray image processing apparatus 30 via the network NW as a calculation resource, thereby implementing the functions shown in FIG. 8.

The term "processor" used in the above description means, for example, a circuit such as a CPU, a GPU (Graphics processing Unit), an ASIC (Application Specific Integrated Circuit), or a programmable logic device (for example, an SPLD (Simple Programmable Logic Device), a CPLD (Complex Programmable Logic Device), and an FPGA (Field Programmable Gate Array)). If the processor is, for example, a CPU, the processor reads out a program stored in a storage circuit and executes it, thereby implementing a function. On the other hand, if the processor is, for example, an ASIC, instead of storing the program in the storage circuit, the function is directly incorporated in the circuit of the processor. Note that the processor according to each embodiment need not necessarily be configured as a single circuit for each processor. Instead, one processor may be formed by combining a plurality of independent circuits to implement the functions. Also, a plurality of constituent elements shown in the drawings may be integrated into one processor to implement the functions.

It has been described above that the single memory 33 stores the programs corresponding to the processing functions of the processing circuit 35. It has also been described above that the single memory 108 stores the programs corresponding to the processing functions of the processing circuit 110. However, the embodiment is not limited to this. For example, a plurality of memories 33 may be distributively arranged, and the processing circuit 35 may be configured to read out the corresponding programs from the individual memories 33. Similarly, a plurality of memories 108 may be distributively arranged, and the processing circuit 110 may be configured to read out the corresponding programs from the individual memories 108. Instead of storing the programs in the memory 33 or the memory 108, the programs may directly be incorporated in the circuit of the processor. In this case, the processor reads out and executes the programs incorporated in the circuit, thereby implementing the functions.

The constituent elements of each apparatus according to the above-described embodiments are functional and conceptual, and need not always physically be configured as shown in the drawings. That is, the detailed form of distribution/integration of the apparatuses is not limited to that illustrated, and all or some of the apparatuses can be distributed/integrated functionally or physically in an arbitrary unit in accordance with various kinds of loads and use conditions. Also, all or some arbitrary processing functions performed in each apparatus may be implemented by a CPU and programs analyzed and executed by the CPU, or may be implemented as hardware by a wired logic.

In addition, each method described in the above-described embodiments can be implemented by a computer such as a personal computer or a workstation executing a program prepared in advance. The program can be distributed via a network such as the Internet. The medical image processing program may be recorded in a non-transitory computer-readable recording medium such as a hard disk, a flexible disk (FD), a CD-ROM, an MO, or a DVD and read out from the recording medium and executed by the computer.

According to at least one embodiment described above, it is possible to improve the accuracy of gain correction.

Several embodiments have been described above. These embodiments are merely examples and are not intended to limit the scope of the present disclosure. These embodiments can be executed in various other forms, and various omissions, replacements, changes, and combinations of the embodiments can be made without departing from the scope of the appended claims. These embodiments and modifications are incorporated in the scope of the present disclosure, and are also described in the claims and their equivalents.

Concerning the above-described embodiments, the following supplementary notes are disclosed as the aspects and selective features of the present disclosure.

(Supplementary Note 1)

There is provided an X-ray image processing apparatus comprising:
　a first obtaining unit configured to obtain a first X-ray image including an object;
　a second obtaining unit configured to obtain a first measured value associated with an X-ray condition of the first X-ray image, a second X-ray image that does not include the object, and a second measured value associated with an X-ray condition of the second X-ray image;
　a gain correction unit configured to correct the first X-ray image based on the first measured value, the second X-ray image, and the second measured value; and
　an image generation unit configured to generate an evaluation image for evaluating a state of the object based on the corrected image corrected by the gain correction unit.

(Supplementary Note 2)

The gain correction unit may
　correct the first X-ray image corresponding to high energy of two different types of energies based on the first measured value, the second X-ray image, and the second measured value corresponding to X-rays of the high energy,
　correct the first X-ray image corresponding to low energy of the two types of energies based on the first measured value, the second X-ray image, and the second measured value corresponding to X-rays of the low energy, and
　obtain a first corrected image corresponding to the X-rays of the high energy and a second corrected image corresponding to the X-rays of the low energy, and
　the image generation unit may generate the evaluation image based on the first corrected image and the second corrected image.

(Supplementary Note 3)

The image generation unit may perform logarithmic transformation of the first corrected image and the second corrected image, multiply one of the corrected images that have undergone the logarithmic transformation by a predetermined coefficient, and generate the evaluation image based on the corrected image multiplied by the coefficient and the other corrected image that has undergone the logarithmic transformation.

(Supplementary Note 4)

The first measured value and the second measured value may be waveform data of a tube current.

(Supplementary Note 5)

An X-ray image without the object and a measured value associated with an X-ray condition of the X-ray image may be stored in a memory in association with each of a plurality of energies, and the second obtaining unit may obtain, from the memory, the second X-ray image and the second measured value in accordance with the X-ray condition set for the object.

(Supplementary Note 6)

The apparatus may further comprise an index measurement unit configured to measure, based on the evaluation image generated by the image generation unit, an index for evaluating the state of the object.

(Supplementary Note 7)

The index measurement unit may obtain a calibration curve according to a tube voltage associated with the X-ray condition of the first X-ray image, and measure the index based on the obtained calibration curve and the evaluation image.

(Supplementary Note 8)

There is provided an X-ray diagnosis apparatus comprising:

a first obtaining unit configured to obtain a first X-ray image including an object;

a second obtaining unit configured to obtain a first measured value associated with an X-ray condition of the first X-ray image, a second X-ray image that does not include the object, and a second measured value associated with an X-ray condition of the second X-ray image;

a gain correction unit configured to correct the first X-ray image based on the first measured value, the second X-ray image, and the second measured value; and an image generation unit configured to generate an evaluation image for evaluating a state of the object based on a corrected image that is the first X-ray image corrected by the gain correction unit.

(Supplementary Note 9)

There is provided a method comprising:

obtaining a first X-ray image including an object;

obtaining a first measured value associated with an X-ray condition of the first X-ray image, a second X-ray image that does not include the object, and a second measured value associated with an X-ray condition of the second X-ray image;

correcting the first X-ray image based on the first measured value, the second X-ray image, and the second measured value; and generating an evaluation image for evaluating a state of the object based on a corrected image that is the corrected first X-ray image.

(Supplementary Note 10)

There is provided a program configured to cause a computer to execute each of processes of:

obtaining a first X-ray image including an object;

obtaining a first measured value associated with an X-ray condition of the first X-ray image, a second X-ray image that does not include the object, and a second measured value associated with an X-ray condition of the second X-ray image;

correcting the first X-ray image based on the first measured value, the second X-ray image, and the second measured value; and generating an evaluation image for evaluating a state of the object based on a corrected image that is the corrected first X-ray image.

(Supplementary Note 11)

The image generation unit may generate, as the evaluation image, a bone image representing a bone of the object.

(Supplementary Note 12)

The index measurement unit may execute analysis processing based on the bone image and calculate a bone mineral density.

(Supplementary Note 13)

The image generation unit may generate, as the evaluation image, a mammary gland image representing a mammary gland of the object.

(Supplementary Note 14)

The index measurement unit may execute analysis processing based on the mammary gland image and calculate a breast density.

(Supplementary Note 15)

The X-ray condition may include a measured value of at least one of a tube voltage, a tube current, and a pulse width.

(Supplementary Note 16)

The gain correction unit may calculate, as the X-ray condition, a measured value of a tube current based on data of an area dosimeter, a measured value of a tube voltage, and a measured value of a pulse width.

(Supplementary Note 17)

In accordance with the X-ray condition when an object image is captured, the gain correction unit may select a gain image from a plurality of preliminary gain images each captured for each set value of a tube current.

Other Embodiments

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the specification is not limited to the disclosed exemplary embodiments. The scope of the following claims is to be accorded the broadest interpretation so as to encompass all such modifications and equivalent structures and functions.

This application claims the benefit of Japanese Patent Application No. 2021-165048, filed Oct. 6, 2021, which is hereby incorporated by reference herein in its entirety.

What is claimed is:

1. An X-ray image processing apparatus comprising:
at least one of (a) one or more processors connected to one or more memories storing a program including instructions executed by the one or more processors and (b) circuitry configured to function as:
a first obtaining unit configured to obtain a first X-ray image including an object;
a second obtaining unit configured to obtain a first measured value associated with an X-ray condition of the first X-ray image, a second X-ray image that does not include the object, and a second measured value associated with an X-ray condition of the second X-ray image;
a gain correction unit configured to correct the first X-ray image corresponding to high energy of two different types of energies based on the first measured value corresponding to the high energy, the second X-ray image corresponding to the high energy, and the second measured value corresponding the high energy, and correct the first X-ray image corresponding to low energy of the two types of energies based on the first measured value corresponding to the low energy, the second X-ray image corresponding to the low energy, and the second measured value corresponding to the low energy; and
an image generation unit configured to generate an evaluation image for evaluating a state of the object based on the corrected first X-ray image corresponding to the high energy and the corrected first X-ray image corresponding to the low energy.

2. The apparatus according to claim 1, wherein the image generation unit performs logarithmic transformation of the first corrected image and the second corrected image, multiplies one of the corrected images that have undergone the logarithmic transformation by a predetermined coefficient, and generates the evaluation image based on the corrected image multiplied by the coefficient and the other corrected image that has undergone the logarithmic transformation.

3. The apparatus according to claim 1, wherein the first measured value and the second measured value are waveform data of a tube current.

4. The apparatus according to claim 1, wherein
an X-ray image without the object and a measured value associated with an X-ray condition of the X-ray image are stored in a memory in association with each of a plurality of energies, and
the second obtaining unit obtains, from the memory, the second X-ray image and the second measured value in accordance with the X-ray condition set for the object.

5. The apparatus according to claim 1, wherein the at least one of (a) the one or more processors connected to the one or more memories storing the program including the instructions executed by the one or more processors and (b) the circuitry are further configured to function as an index measurement unit configured to measure, based on the evaluation image generated by the image generation unit, an index for evaluating the state of the object.

6. The apparatus according to claim 5, wherein the index measurement unit obtains a calibration curve according to a tube voltage associated with the X-ray condition of the first X-ray image, and measures the index based on the obtained calibration curve and the evaluation image.

7. The apparatus according to claim 5, wherein the index measurement unit executes analysis processing based on a bone image representing a bone of the object and calculates a bone mineral density.

8. The apparatus according to claim 5, wherein the index measurement unit executes analysis processing based on a mammary gland image representing a mammary gland of the object and calculates a breast density.

9. The apparatus according to claim 1, wherein the image generation unit generates, as the evaluation image, a bone image representing a bone of the object.

10. The apparatus according to claim 1, wherein the image generation unit generates, as the evaluation image, a mammary gland image representing a mammary gland of the object.

11. The apparatus according to claim 1, wherein the X-ray condition includes a measured value of at least one of a tube voltage, a tube current, and a pulse width.

12. The apparatus according to claim 1, wherein the gain correction unit calculates, as the X-ray condition, a measured value of a tube current based on data of an area dosimeter, a measured value of a tube voltage, and a measured value of a pulse width.

13. The apparatus according to claim 1, wherein in accordance with the X-ray condition when an object image is captured, the gain correction unit selects a gain image from a plurality of preliminary gain images each captured for each set value of a tube current.

14. An X-ray diagnosis apparatus comprising:
at least one of (a) one or more processors connected to one or more memories storing a program including instructions executed by the one or more processors and (b) circuitry configured to function as:
a first obtaining unit configured to obtain a first X-ray image including an object;
a second obtaining unit configured to obtain a first measured value associated with an X-ray condition of the first X-ray image, a second X-ray image that does not include the object, and a second measured value associated with an X-ray condition of the second X-ray image;
a gain correction unit configured to correct the first X-ray image corresponding to high energy of two different types of energies based on the first measured value corresponding to the high energy, the second X-ray image corresponding to the high energy, and the second measured value corresponding the high energy, and correct the first X-ray image corresponding to low energy of the two types of energies based on the first measured value corresponding to the low energy, the second X-ray image corresponding to the low energy, and the second measured value corresponding to the low energy; and
an image generation unit configured to generate an evaluation image for evaluating a state of the object based on the corrected first X-ray image corresponding to the high energy and the corrected first X-ray image corresponding to the low energy.

15. A method comprising:
obtaining a first X-ray image including an object;
obtaining a first measured value associated with an X-ray condition of the first X-ray image, a second X-ray image that does not include the object, and a second measured value associated with an X-ray condition of the second X-ray image;

correcting the first X-ray image corresponding to high energy of two different types of energies based on the first measured value corresponding to the high energy, the second X-ray image corresponding to the high energy, and the second measured value corresponding the high energy, and correcting the first X-ray image corresponding to low energy of the two types of energies based on the first measured value corresponding to the low energy, the second X-ray image corresponding to the low energy, and the second measured value corresponding to the low energy; and generating an evaluation image for evaluating a state of the object based on the corrected first X-ray image corresponding to the high energy and the corrected first X-ray image corresponding to the low energy.

16. A non-transitory computer-readable storage medium storing a program for causing a computer to execute a method comprising:

obtaining a first X-ray image including an object;

obtaining a first measured value associated with an X-ray condition of the first X-ray image, a second X-ray image that does not include the object, and a second measured value associated with an X-ray condition of the second X-ray image;

correcting the first X-ray image corresponding to high energy of two different types of energies based on the first measured value corresponding to the high energy, the second X-ray image corresponding to the high energy, and the second measured value corresponding the high energy, and correcting the first X-ray image corresponding to low energy of the two types of energies based on the first measured value corresponding to the low energy, the second X-ray image corresponding to the low energy, and the second measured value corresponding to the low energy; and generating an evaluation image for evaluating a state of the object based on the corrected first X-ray image corresponding to the high energy and the corrected first X-ray image corresponding to the low energy.

\* \* \* \* \*